United States Patent
Metzger et al.

(10) Patent No.: US 6,303,114 B1
(45) Date of Patent: Oct. 16, 2001

(54) IL-12 ENHANCEMENT OF IMMUNE RESPONSES TO T-INDEPENDENT ANTIGENS

(75) Inventors: Dennis W. Metzger, Sylvania; Renee M. Buchanan, Toledo, both of OH (US)

(73) Assignee: The Medical College of Ohio, Toledo, OH (US)

( * ) Notice: Subject to any disclaimer, the term of this patent is extended or adjusted under 35 U.S.C. 154(b) by 0 days.

(21) Appl. No.: 09/035,594

(22) Filed: Mar. 5, 1998

(51) Int. Cl.$^7$ .................................................. A61K 38/20

(52) U.S. Cl. .................. 424/85.2; 424/184.1; 424/190.1; 424/198.1; 514/2; 514/8; 514/12; 514/54; 514/885

(58) Field of Search .................................. 424/85.1, 85.2, 424/184.1, 190.1, 198.1; 514/2, 8, 12, 54, 885

(56) References Cited

U.S. PATENT DOCUMENTS 5,723,127 * 3/1998 Scott et al. ......................... 424/184.1

FOREIGN PATENT DOCUMENTS

WO 97/45139    12/1997  (WO) .

OTHER PUBLICATIONS

White et al. (1991) in Advances in Experimental Medicine & Biology, Immunology of Proteins & Peptides VI Edited by M.Z. Atassi, Plunum Press, N.Y. pp. 207–210, vol. 303.*
Mongini et al. (1982) J. of Enptal Medicine. vol. 155, pp. 884–902.*
Westerink, M.A.J., et al., "Primary Human Immune Response to Neisseria meningitidis Serogroup C in Interleukin–12–Treated Severe Combined Immunodeficient Mice Engrafted with Human Peripheral Blood Lymphocytes," J. Infect. Dis., 175:84–90 (1997).
Ying–zi, C., et al., "Treatment of Murine CD5⁻ B Cells with Anti–Ig, but not LPS, Induces Surface CD5: Two B–cell Activation Pathways," Int. Immunol., 3(5):467–476 (1991).
Riggs, J.E., et al., "The Immunoglobulin Allotype Contributed by Peritoneal Cavity B Bells Dominates in SCID Mice Reconstituted with Allotype–disparate Mixtures of Splenic and Peritoneal Cavity B Cells," J. Exp. Med., 172:475–485 (1990).
Vogel, L.A., et al., "Inhibition of Murine B1 Lymphocytes by Interleukin–12," Eur. J. Immunol., 26:219–223 (1996).
Velupillai, P., et al., "Interleukin–12 and –10 and Gamma Interferon Regulate Polyclonal and Ligand–Specific Expansion of Murine B–1 Cells," Infection and Immunity, 64(11):4557–4560 (1996).
Wilder, J.A., et al., "The Role of NK Cells During In Vivo Antigen–Specific Antibody Responses," J. Immunol., 156:146–152 (1996).

Snapper, C.M., et al., "An In Vitro Model for T Cell–Independent Induction of Humoral Immunity," J. Immunol., 152:4884–4892 (1994).
Snapper, C.M. and Mond, J.J., "A Model for Induction of T Cell–Independent Humoral Immunity in Response to Polysaccharide Antigens," J. Immunol., 157:2229–2233 (1996).
Koh, C. Y. and Yuan, D., "The Effect of NK Cell Activation by Tumor Cells on Antigen–Specific Antibody Responses," J. Immunol., 159:47454752 (1997).
Snapper, C.M. and Paul, W.E., "Interferon–γ and B Cell Stimulatory Factor–1 Reciprocally Regulate Ig Isotype Production," Science, 236:944–947 (1987).
Snapper, C.M. et al., "Induction of IgG3 Secretion by Interferon γ: A Model for T Cell–independent Class Switching in Response to T Cell–independent Type 2 Antigens," J. Exp. Med., 175:1367–1371 (1992).
Collins, J.T. and Dunnick, W.A., "Germline Transcripts of the Murine Immunoglobulin γ2a Gene: Structure and Induction by IFN–γ," Int. Immunol., 5(8):885–891 (1993).
Pang, Y., et al., "Interferon–γ Gene Expression in Human B–Cell Lines: Induction by Interleukin–2, Protein Kinase C Activators, and Possible Effect of Hypomethylation on Gene Regulation," Blood, 80(3):724–732 (1992).
Buschle, M., et al., "Interferon γ Inhibits Apoptotic Cell Death in B Cell Chronic Lymphocytic Leukemia," J. Exp. Med., 177:213–218 (1993).
Yoshimoto, T., et al., "Interleukin 18 Together with Interleukin 12 Inhibits IgE Production by Induction of Interferon–γ Production from Activated B Cells," Proc. Natl. Acad. Sci., USA, 94:3948–3953 (1997).
Robbins, J.B., et al., "Perspective: Hypothesis: Serum IgG Antibody is Sufficient to Confer Protection Against Infectious Diseases by Inactivating the Inoculum," J. Inf. Dis., 171:1387–1398 (1995).
Robbins, J.B., et al., "Hypothesis: How Licensed Vaccines Confer Protective Immunity," In Novel Strategies in Design and Production of Vaccines, Cohen, S. et al., eds. (NY:Plenum Press) (1996).

(List continued on next page.)

Primary Examiner—Prema Mertz
(74) Attorney, Agent, or Firm—Hamilton, Brook, Smith & Reynolds, P.C.

(57) ABSTRACT

The present invention relates to a method of modulating an immune response to a T-cell or thymus independent antigen in a host (e.g., mammalian, including human), comprising administering to the host an effective amount of interleukin-12 (IL-12) and the T-cell independent antigen. In one embodiment, the present invention relates to a method of inducing an immune response to a TI antigen in a host (e.g., mammalian, including human), which comprises administering to the host an effective amount of interleukin-12 (IL-12) and the TI antigen. In another embodiment, the present invention relates to a method of enhancing an immune response against a TI antigen in a host, which comprises administering to the host an effective amount of IL-12 and the TI antigen. The methods of the present invention can be used, for example, to induce and or enhance a humoral immune response (IgG2a and/or IgG3 humoral immune response).

25 Claims, 11 Drawing Sheets

OTHER PUBLICATIONS

Trinchieri, G., "Interleukin–12: A Proinflammatory Cytokine with Immunoregulatory Functions that Bridge Innate Resistance and Antigen–Specific Adaptive Immunity," *Annu. Rev. Immunol.*, 13:251–276 (1995).

Buchanan, J.M., et al., "Biological Properties and Potential Clinical Applications of Interleukin 12," *Int. J. Pediatric Hematology/Oncology*, 3:123–131 (1996).

Wang, B., et al., "A Block in Both Early T Lymphocyte and Natural Killer Cell Development in Transgenic Mice with High–Copy Numbers of the Human CD3E Gene," *Proc. Natl. Acad. Sci., USA*, 91:9402–9406 (1994).

Bondada, S. and Garg, M., "Thymus–Independent Antigens," In *Handbook of B and T Lymphocytes*, E.C. Snow, ed. Academic Press, p. 343–370 (1994).

Buchanan, J.M., et al., "Interleukin 12 alters the isotype–restricted antibody response of mice to hen eggwhite lysozyme," *Int. Immunol.*, 7:1519–1528 (1995).

Germann, T., et al., "Interleukin–12 profoundly up–regulates the synthesis of antigen–specific complement–fixing IgG2a, IgG2b and IgG3 antibody subclasses in vivo," *Eur. J. Immunol.*, 25:823–829 (1995).

Metzger, D.W., et al., "Interleukin–12 acts as an adjuvant for humoral immunity through inteferon–gamma–dependent and –independent mechanisms," *Eur. J. Immunol.*, 27:1958–1965 (1997).

Mond, J.J., et al., "T Cell independent antigens," *Curr. Opin. Immunol.*, 7:349–354 (1995).

Mond, J.J., et al., "T Cell–independent antigens type 2," *Annu. Rev. Immunol.*, 13:655–692 (1995).

Snapper, C.M., et al., "An in vitro model for T cell–independent induction of humoral immunity. A requirement for NK cells," *J. Immunol.*, 152:4884–4892 (1994).

Wynn, T.A., et al., "Il–12 enhances vaccine–induced immunity to schistosomes by augmenting both humoral and cell–mediated immune responses against the parasite," *J. Immunol.*, 157:4068–4078 (1996).

Buchanan, R.M., et al., "IL–12 Enhances Antibody Responses to T–Independent Polysaccharide Vaccines in the Absence of T and NK Cells", *J. Immunol.*, 161(10):5525–5533 (1998).

Nohria A. & Rubin, R.H., "Cytokines as potential vaccine adjuvants", *Biotherapy*, 7(3–4):261–269 (1994).

Trinchieri, G., "Immunobiology of Interleukin–12", *Immunol. Res.*, 17(1–2):269–278 (1998).

* cited by examiner

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:1:

TGAACGCTAC ACACTGCATC TTGG                    24

(2) INFORMATION FOR SEQ ID NO:2:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:2:

CGACTCCTTT TCCGCTTCCT GAG                     23

(2) INFORMATION FOR SEQ ID NO:3:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "DNA"

(xi) SEQUENCE DESCRIPTION: SEQ ID NO:3:

GTTGGATACA GGCCAGACTT TGTTG                   25

```
-continued (2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:4:

GATTCAACTT GCGCTCATCT TAGGC                                              25
```

IL-12 ENHANCEMENT OF IMMUNE RESPONSES TO T-INDEPENDENT ANTIGENS

GOVERNMENT SUPPORT

The invention was supported, in whole or in part, by grant R21 AI38380 from the National Institutes of Health. The Government has certain rights in the invention.

BACKGROUND OF THE INVENTION

Non-protein antigens such as polysaccharides and lipids induce antibody responses without the need for T cells and are therefore referred to as T-independent (TI) antigens. However, because of the lack of involvement of T cell help, most TI antigens are relatively poor immunogens. In general, responses to TI antigens consist of IgM antibodies of low affinity, and do not show significant heavy chain class switching, affinity maturation, or memory. The practical significance of TI antigens is that many bacterial capsular and cell wall polysaccharides belong to this category and are therefore relatively poor at eliciting humoral immunity.

Young children and the elderly are particularly susceptible to life-threatening infections with encapsulated bacteria such as pneumococcus and meningococcus. It has been estimated by the Centers for Disease Control that in the U.S. per year, Streptococcus pneumoniae causes 3,000 cases of meningitidis, 50,000 cases of bacteremia, 500,000 cases of pneumonia, and 7 million cases of otitis media (middle ear infection). The World Health Organization has estimated that worldwide, this organism causes 100 million cases per year with 10 million deaths per year. Similarly, Neisseria meningiditis is the leading cause of meningitis in children and young adults with 2,600 cases/year in the U.S., 310,000 cases and 35,000 deaths per year worldwide.

Polysaccharide vaccines for inducing immunity to pathogens such as S. pneumoniae and N. meningiditis are available, but they are generally ineffective in children less than 2 years of age and are of limited efficacy in older individuals. In addition, in all recipients the vaccines, even in conjugate form, induce limited isotype switching. Clearly, alternative approaches for vaccination against pathogens having TI antigens are needed.

SUMMARY OF THE INVENTION

Applicants have found that interleukin-12 (IL-12) serves as a very strong adjuvant for eliciting immune responses (e.g., antibody (IgG) response) during T-cell independent (TI) immune responses, including responses to vaccine preparations which are currently used in humans. Thus, the present invention relates to a method of enhancing an immune response against a TI antigen (one or more) in a host. In one embodiment, the present invention relates to a method of inducing an immune response against a TI antigen in a host, which comprises administering to the host an effective amount of IL-12 and the TI antigen. In another embodiment, the present invention is a method of enhancing an immune response against a TI antigen in a host, which comprises administering to the host an effective amount of IL-12 and the TI antigen. The methods of the present invention can be used to induce and/or enhance an immune response to a TI antigen in a mammalian host, such as a primate (e.g., human), murine, feline, canine, bovine or porcine host. The invention also relates to compositions comprising IL-12 and a TI antigen.

The methods of the present invention can be used, for example, to induce and/or enhance a humoral immune response (e.g., IgG2a and/or IgG3 humoral immune response) in the host. The TI antigen can include, for example, a carbohydrate (e.g., a polysaccharide), a lipid, (e.g., liposomes, phosphorylcholine) a glycoprotein, a hapten-carrier conjugate, a lipopolysaccharide, or a phage (e.g., T4). The IL-12 and/or the TI antigen can be administered as a protein or as a polynucleotide under conditions in which the TI antigen and/or IL-12 is expressed in vivo.

In a particular embodiment, the present invention relates to a method of inducing and/or enhancing an immune response to Streptococcus pneumoniae in a host, which comprises administering to the host an effective amount of IL-12 and the TI antigen of Streptococcus pneumoniae. In another embodiment, the invention relates to a method of inducing and/or enhancing an immune response to Neisseria meningiditis in a host, which comprises administering to the host an effective amount of IL-12 and the TI antigen of Neisseria meningiditis.

The invention also encompasses a composition comprising IL-12 and a TI antigen. One or more TI antigens can be used in the methods and compositions of the present invention.

Use of IL-12 as described herein provides effective methods and compositions which can be used to induce and/or enhance an immune response against a TI antigen.

DETAILED DESCRIPTION OF THE INVENTION

Figure 1A:
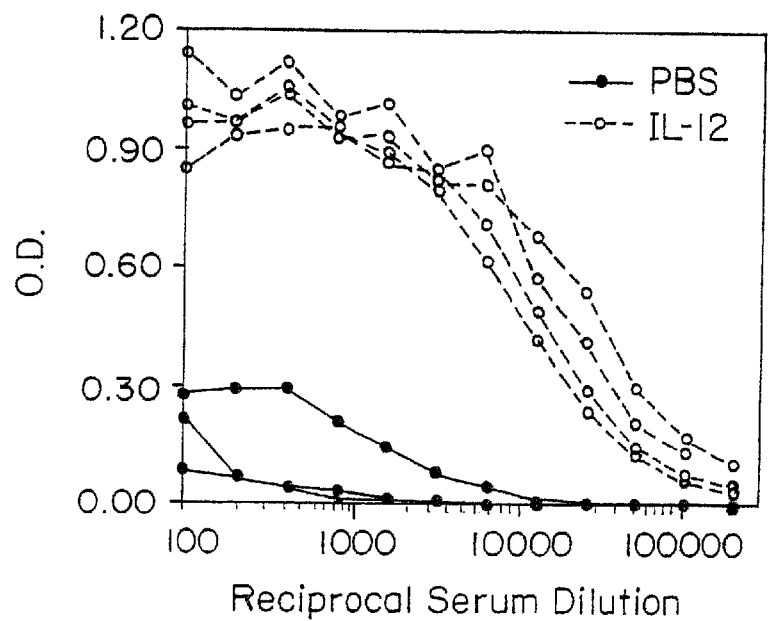
FIGS. 1A–1B are graphs of reciprocal serum dilution versus optical density (O.D.) showing increased levels of dinitrophenyl (DNP)-specific IgG2a (FIG. 1A) and IgG3 (FIG. 1B) in BALB/c mice injected with IL-12 and 50 µg of DNP-ovalbumin (DNP-OVA) (open symbols), a model T cell dependent (TD) antigen, compared to control mice injected with DNP-OVA and phosphate buffered saline (PBS) (closed symbols); each line represents binding of serum from an individual mouse.

Polysaccharide vaccines to encapsulated bacteria such as *Neisseria meningitidis* and *Streptococcus pneumoniae* are weakly immunogenic due to their TI nature. Even when converted to T-dependent forms through conjugation to foreign proteins, polysaccharides induce responses that are deficient in many respects, such as induction of murine IgG2a antibody, the isotype which mediates optimal complement fixation and opsonization. As described herein, IL-12 treatment of mice induced significantly increased levels of IgG2a antibody to a model TI antigen, DNP-Ficoll, and to vaccines composed of polysaccharides from pneumococci and meningococci. Use of immunodeficient mice lacking T cells and/or NK cells demonstrated that such cells were not responsible for the observed antibody enhancement. Furthermore, the use of IFN-γ KO mice showed that stimulation of TI antibody responses by IL-12 was only partially dependent on IFN-γ. The ability of IL-12 to dramatically enhance TI antibody responses shows that IL-12 is useful as a powerful adjuvant to induce protective immune responses against encapsulated pathogens.

The present invention relates to a method of enhancing an immune response against a TI antigen in a host. In one embodiment, the present invention relates to a method of inducing an immune response against a TI antigen (one or more) in a host, which comprises administering to the host an effective amount of IL-12 and the TI antigen. In another embodiment, the present invention is a method of enhancing an immune response against a TI antigen in a host, which comprises administering to the host an effective amount of IL-12 and the TI antigen.

As used herein, the terms "enhance" and/or "enhancing" refer to the strengthening (augmenting) of an existing immune response to a pathogen. The term also refers to the initiation of (initiating, inducing) an immune response to a pathogen.

As used herein a "T-cell independent (TI) antigen", also referred to herein as a "thymus-independent antigen", is an antigen which is capable of inducing an immune response in a host without the need for mature T-cells. Therefore, TI antigens include antigens recognized by immature T cells (e.g., CD1 molecules), such as lipoarabinomannan. TI antigens also include, for example, carbohydrates (e.g., polysaccharides), lipids, glycolipids, carrier conjugates (e.g., *H. influenza* conjugate vaccine, polysaccharide conjugate, lipid conjugate, phage conjugate), lipopolysaccharides and phages (see, for example, Bondada and M. Grag, "Thymus-Independent Antigens" in *The Handbook of B and T Lymphocytes*, E. Charles Snow, Academic Press, Inc., San Diego, (1994) pages 343–370). Particular examples of TI antigens include bacterial polysaccharides, such as bacterial capsular polysaccharides (e.g., *Streptococcus pneumoniae* capsular polysaccharide, such as the PNU-Immune 23 vaccine, *Neisseria meningiditis* A, C, Y and W-135 serogroups), and bacterial cell wall polysaccharides (e.g., streptococcal carbohydrates, phosphorylcholine), liposomes, phosphorylcholine and T4.

The TI antigen can be obtained or derived from a variety of pathogens or organisms, such as encapsulated organisms (e.g., bacteria such as *S. pneumoniae*, *N. meningiditis*, *Haemophilus influenzae*, *Brucella abortis*), viruses (e.g., T4 phage), parasites, fungi and yeast, against which an immune response is desired. The TI antigen of a pathogen can be obtained using skills known in the art. For example, the TI antigen can be isolated (purified, essentially pure) directly from a pathogen, derived using chemical synthesis or obtained using recombinant methodology. In addition, the TI antigen can be obtained from commercial sources, as described in the exemplification.

IL-12 is a recently characterized heterodimeric cytokine that has a molecular weight of 75 kDa and is composed of disulfide-bonded 40 kDa and 35 kDa subunits. It is produced by antigen presenting cells such as macrophages, and binds to receptors on activated T, B and NK cells (Desai, B. B., et al., *J. Immunol.*, 148:3125–3132 (1992); Vogel, L.A., et al., *Int. Immunol.*, 8:1955–1962 (1996)). It has several effects including 1) enhanced proliferation of T cells and NK cells, 2) increased cytolytic activities of T cells, NK cells, and macrophages, 3) induction of IFN-γ production and to a lesser extent, TNF-α and GM-CSF, and 4) activation of TH1 cells (Trinchieri, G., et al., *Blood*, 84:4008–4027 (1994). IL-12 has been shown to be an important costimulator of proliferation in Th1 clones (Kennedy et al., *Eur. J. Immunol.* 24:2271–2278, 1994) and leads to increased production of IgG2a antibodies in serum (Morris, S. C., et al., *J. Immunol.* 152:1047 (1994); Germann, T. M., et al., *Eur. J. Immunol.*, 25:823–829 (1995); Sher, A., et al., *Ann. N.Y. Acad. Sci.*, 795:202–207 (1996); Buchanan, J. M., et al., *Int. Imm.*, 7:1519–1528 (1995); Metzger, D. W., et al., *Eur. J. Immunol.*, 27:1958–1965 (1997)). Administration of IL-12 can also temporarily decrease production of IgG1 antibodies (Morris, S. C., et al., *J. Immunol.* 152:1047 (1994); McKnight, A. J., *J. Immunol.* 152:2172 (1994); Buchanan, J. M., et al., *Int. Imm.*, 7:1519–1528 (1995)), indicating suppression of the Th2 response. The purification and cloning of IL-12 are disclosed in PCT publication nos. WO 92/05256 and WO 90/05147, and in European patent publication no. 322,827 (identified as "CLMF").

As used herein, "interleukin-12" and "IL-12" refer to interleukin-12 protein, its individual subunits, multimers of its individual subunits, functional fragments or portions of IL-12, and functional equivalents and/or analogues of "interleukin-12" and "IL-12". As defined herein, functional fragments of IL-12 are fragments which modulate an immune response against a TI antigen in a host. As also defined herein, functional equivalents or fragments of "interleukin-12" and "IL-12" include modified IL-12 protein such that the resulting IL-12 product has activity similar to the IL-12 described herein (e.g., inducing and/or enhancing an immune response to a TI antigen). Functional equivalents or fragments of "interleukin-12" also include nucleic acid sequences (e.g., DNA, RNA) and portions thereof, which encode a protein or peptide having the IL-12 function or activity (e.g., inducing and/or enhancing an immune response to a TI antigen). In addition, the term includes a nucleotide sequence which through the degeneracy of the genetic code encodes a similar peptide gene product as IL-12 and has the IL-12 activity described herein. For example, a functional equivalent of "interleukin-12" and "IL-12" includes a nucleotide sequence which contains a "silent" codon substitution (e.g., substitution of one codon encoding an amino acid for another codon encoding the same amino acid) or an amino acid sequence which contains a "silent" amino acid substitution (e.g., substitution of one acidic amino acid for another acidic amino acid).

IL-12 suitable for use in the methods and compositions of the present invention can be obtained from a variety of sources or synthesized using skills known in the art. For example, IL-12 can be purified (isolated, essentially pure) from natural sources (e.g., mammalian sources, such as murine or human sources), produced by chemical synthesis or produced by recombinant DNA techniques. In addition, the IL-12 can be obtained from commercial sources.

An effective amount of IL-12 is administered in the methods of the present invention which is an amount that induces and/or enhances an immune response to a TI antigen in the host. Thus, as used herein, "an effective amount of IL-12" is an amount such that when administered to a host, it results in an immune response or an enhanced immune response to the TI antigen in the host relative to the immune response to the TI antigen in a host when an effective amount of IL-12 is not administered to a host. That is, an "effective amount" of IL-12 is an amount that induces and/or enhances an immune response to a TI antigen relative to the immune response to the TI antigen if IL-12 is not administered.

The IL-12 and the TI antigen can be administered as a prophylactic vaccine or a therapeutic vaccine. That is, the IL-12 can be administered either before (to prevent) or after (to treat) the effects of a pathogen having a TI antigen which has appeared and/or manifested in a host. Thus, the IL-12 can be administered to a host who either exhibits the disease state caused by a pathogen from which the TI antigen is obtained or derived, or does not yet exhibit the disease state caused by a pathogen from which the TI antigen is obtained or derived. Thus, the IL-12 and TI antigen can be administered to hosts either before or after the disease state is manifested in the host and can result in prevention, amelioration, elimination or a delay in the onset of the disease state caused by the pathogen from which the TI antigen is obtained or derived.

The IL-12 and the TI antigen can be administered to a host in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the IL-12 and/or TI antigen can be administered together with other components or biologically active agents, such as adjuvants (e.g., alum), pharmaceutically acceptable surfactants (e.g., glycerides), excipients (e.g., lactose), carriers, diluents, liposomes and vehicles. If desired, certain sweetening, flavoring and/or coloring agents can also be added.

Further, the IL-12 and/or the TI antigen can be administered by in vivo expression of polynucleotides encoding such into a mammalian subject. For example, the IL-12 and/or TI antigen can be administered to a host using a live vector, wherein the live vector containing IL-12 and/or TI antigen nucleic acid sequences are administered under conditions in which the IL-12 and/or TI antigen are expressed in vivo. For example, a host can be injected with a vector which encodes and expresses a TI antigen in vivo in combination with IL-12 protein or peptide, or in combination with a vector which encodes and expresses IL-12 protein in vivo. Alternatively, a host can be injected with a vector which encodes and expresses IL-12 in vivo in combination with a TI antigen conjugated to a peptide or protein form or a mimic of a protein or peptide form, or in combination with a vector which encodes and expresses a TI antigen. A single vector containing the sequences encoding a TI antigen and the IL-12 protein are also useful in the methods of the present invention.

Several expression vector systems are available commercially or can be reproduced according to recombinant DNA and cell culture techniques. For example, vector systems such as the yeast or vaccinia virus expression systems, or virus vectors can be used in the methods and compositions of the present invention (Kaufman, R. J., *A J. of Meth. in Cell and Molec. Biol.*, 2:221–236 (1990)). Other techniques using naked plasmids or DNA, and cloned genes encapsulated in targeted liposomes or in erythrocyte ghosts, can be used to introduce IL-12 and/or TI antigen polynucleotides into the host (Freidman, T., *Science*, 244:1275–1281 (1991); Rabinovich, N. R., et al., *Science*, 12265:1401–1404 (1994)). The construction of expression vectors and the transfer of vectors and nucleic acids into various host cells can be accomplished using genetic engineering techniques, as described in manuals like *Molecular Cloning and Current Protocols in Molecular Biology*, which are hereby incorporated by reference, or by using commercially available kits (Sambrook, J., et al., *Molecular Cloning*, Cold Spring Harbor Press, 1989; Ausubel, F. M., et al., *Current Protocols in Molecular Biology*, Greene Publishing Associates and Wiley-Interscience, 1989).

As described herein, administration of IL-12 and a TI antigen elicits or enhances an immune response in the recipient host. In particular, a humoral immune response against the TI antigen is induced or enhanced in the host. In one embodiment, the humoral immune response produced by administration of IL-12 and a TI antigen results in enhanced levels of total antibody in the recipient host compared to a host which does not receive IL-12 and the TI antigen. In another embodiment, the humoral immune response produced by administration of IL-12 and a TI antigen results in production of TI-specific antibody in the host. In a particular embodiment, the TI-specific antibody response produces specific IgG2a and/or IgG3 antibody in the recipient host. As shown in the examples, IL-12 is particularly active in enhancing production of IgG2a, the antibody isotype that is most effective in complement fixation and opsinophagocytosis, the two mechanisms that are most effective in bacterial elimination. It is likely that IL-12 induces or enhances other antibody isotypes such as IgA and IgM.

The immune response to the TI antigen in the host can be due to a general enhanced humoral immune response and/or due to a specific humoral immune response to the TI antigen. In the methods of inducing or enhancing an immune response to a TI antigen in a host, an effective therapeutic amount of IL-12 is administered to the host, which is an amount that induces or enhances an immune response to the TI antigen in the host and results in the improved condition of the host (i.e., the disease or disorder caused by the presence of the pathogen from which the TI antigen is obtained or derived, is prevented, eliminated or diminished). The amount of IL-12 used to induce or enhance an immune response to a TI antigen in a host will vary depending on a variety of factors, including the size, age, body weight, general health, sex and diet of the host, and the time of administration, duration or particular qualities of the disease state. Suitable dose ranges of IL-12 are generally about 0.5

μg to about 150 μg per kg body weight. In one embodiment, the dose range is from about 2.75 μg to about 100 μg per kg body weight. In another embodiment, the dose range is from about 5 μg to about 50 μg per kg body weight. Effective dosages may be extrapolated from dose-response curves derived in vitro or animal model test systems.

In the methods of the present invention, an effective amount of IL-12 is administered in combination with a TI antigen. That is, the IL-12 is administered at a time closely related to immunization of the host with a TI antigen, so that an immune response to the TI antigen is induced or enhanced in the host relative to the immunization of a host in which IL-12 is not administered. Thus, the IL-12 can be administered prior to, preferably just prior to, immunization; at the time of immunization (i.e., simultaneously); or after immunization (subsequently). In addition, the IL-12 can be administered prior to immunization with the TI antigen followed by subsequent administrations of IL-12 after immunization with the TI antigen.

As described herein, IL-12 is capable of dramatically enhancing TI antibody responses in a manner similar to its effects on TD responses. Using DNP-Ficoll and bacterial polysaccharides as model TI antigens, it was found that IgG2a and IgG3 antibody responses were particularly stimulated by IL-12. Surprisingly, enhancement was observed in mice deficient in both T and NK cells. Furthermore, enhancement of IgG3 antibody expression occurred independently from IFN-γ and enhancement of IgG2a expression was only partially dependent on IFN-γ (see the Table). The results demonstrate that IL-12 is useful for inducing protective responses against bacterial pathogens.

IL-12 was found to have similar effects on TD and TI responses to the DNP hapten. In both cases, specific IgG2a and IgG3 anti-DNP serum levels were significantly increased by simultaneous administration of antigen and IL-12 while IgG1 expression was not affected at the time points analyzed. Use of TCROβ⁻δ⁻ double KO mice confirmed the TI nature of the response to DNP-Ficoll and the fact that the mechanism for IL-12 mediated enhancement did not involve T cells. However, the observed effects of the IL-12 in the responses of both WT and TCR KO mice to DNP-Ficoll was of a lesser magnitude than that observed in WT mice against DNP-OVA. This likely reflects a property of the individual DNP-Ficoll preparation rather than the fact that it is a TI antigen since the use of other TI antigens such as bacterial capsular polysaccharides yielded levels of IL-12 enhancement similar to those seen with TD antigens (Germann, T., et al., *Eur. J. Immunol.*, 25:823–829 (1995); Buchanan, J. M., et al., *Int. Immunol.*, 7:1519–1528 (1995)). It has also been recently demonstrated that SCID mice reconstituted with human peripheral blood lymphocytes could mount primary antibody responses to *N. meningitidis* serogroup C polysaccharide if the mice were treated with human IL-12 at the time of cell transfer (Westerink, M. A., et al., *J. Infect. Dis.*, 175:84–90 (1997)). However, in those experiments, it was unclear whether IL-12 was actually stimulating specific antibody-producing B cells or simply aiding in engraftment of the transferred population. It was previously established that IL-12 enhances in vivo TD production of IgG2a in response to protein and haptencarrier antigens (Morris, S. C., et al., *J. Immunol.*, 152:1047–1056 (1994); Germann, T., et al., *Eur. J. Immunol.*, 25:823–829 (1995); Buchanan, J. M., et al., *Int. Immunol.*, 7:1519–1528 (1995); Wynn, T. A., et al., *J. Immunol.*, 157:4068–4078 (1996); Bliss, J., et al., *J. Immunol.*, 156:887–894 (1996); Metzger, D. W., et al., *Eur. J. Immuunol.*, 27:1958–1965 (1997)). Administration of the cytokine suppress IgG1 production but this suppression is only temporary and IgG1 production is also eventually somewhat enhanced (Germann, T., et al., *Eur. J. Immunol.*, 25:823–829 (1995); Buchanan, J. M., et al., *Int. Immunol.*, 7:1519–1528 (1995)). While TD antigens stimulate conventional B cells, TI antigens are thought to preferentially activate cells with the B-1 phenotype (Cong, Y. Z., et al., *Int. Immunol.*, 3:467–476 (1991) and fail to induce isotype switching. Since B-1 cells inhibit responses by conventional B cells (Riggs, J. E., et al., *J. Exp. Med.*, 172:475–485 (1990)) and IL-12 inhibits B-1 cell function (Vogel, L. A., et al., *Eur. J. Immunol.*, 26:219–223 (1996); Velupillai, P., et al., *Infect. Immun.*, 64:4557–4560 (1996)), one influence of IL-12 may be in allowing conventional B cells to respond to TI antigens, thus resulting in the observed enhancement of IgG production.

Several groups have reported that NK cells play a major role in the stimulation of IgG TI responses through release of IFN-δ. It has been shown that Ig secretion induced in vivo or in vitro in a TI manner can be increased by NK cell activation (Wilder, J. A., et al., *J. Immunol.*, 156:146–152 (1996)) and inhibited by NK cell depletion (Snapper, C. M., et al., *J. Immunol.*, 152:4884–4892 (1994); Wilder, J. A., et al., *J. Immunol.*, 156:146–152 (1996)). Antibody neutralization of IFN-γ reverses the influence of NK cells (Snapper, V. M., et al., *J. Immunol.*, 157:2229–2233 (1996). Recently, a role for endogenous IL-12 in TI responses was proposed by Koh and Yuan (Koh, C. Y. and Yuan, D., *J. Immunol.*, 159:4745–4752 (1997) based on the finding that antibody responses induced by TNP-LPS and BCL₁ tumor cells were inhibited by neutralization of IL-12. Since IL-12 is a known activator of NK cells, the role of these cells in IL-12 mediated enhancement of TI antibody responses was investigated. For this purpose mice that are transgenic for the human CD3ε gene and which lack T and NK cells were used. It was found that exposure of these animals to a TI antigen in the presence of IL-12 resulted in enhancement of IgG2a and IgG3 antibody responses. Thus, as described herein, NK cells are not required for stimulation of TI IgG production by IL-12. However, NK cells do appear to be important in maintaining IL-12-induced IgG expression over an extended period of time. While WT and CD3ε mice showed no differences in responsiveness to IL-12 on day 14 after immunization, CD3ε mice did demonstrate lower IgG2a responses compared to WT mice on day 28 and thereafter. Therefore, although NK cells are not strictly required for IL-12's influence, they could be critical depending upon the time of experimental observation.

IFN-γ is known to be a switch for both IgG2a and IgG3 (Buchanan, J. M., et al., *Int. Immunol.*, 7:1519–1528 (1995); Snapper, C. M., et al., *J. Exp. Med.*, 175:1367–1371 (1992); Metzger, D. W., et al., *Eur. J. Immunol.*, 27:1958–1965 (1997); Snapper, C. M., et al., *Science*, 236:944–947 (1987); Collins, J. T., et al., *Int. Immunol.*, 5:885–891 (1993)), the major isotypes induced by IL-12, and high levels of IFN-γ mRNA were detected in the spleens of mice injected with TI antigen and IL-12. Nevertheless, in the absence of the two cell types responsible for IFN-γ production (T and NK cells), IL-12 still significantly enhanced TI antibody responses. This suggests that IFN-γ either is not involved in IL-12 -mediated enhancement of TI antibody responses or is being produced by another cell type. B cells have been reported to produce IFN-γ particularly after stimulation with IL-12 and IL-18 (Pang,Y. Y., et al., *Blood*, 80:724–732 (1992); Buschle, M. D., et al., *J. Exp. Med.*, 177:213–218 (1993); Yoshimoto, T., et al., *Proc. Natl. Acad. Sci.*, USA, 94:3948–3953 (1997)). Furthermore, IFN-γ mRNA has been detected in CD3ε spleen cells that have been activated in vitro with LPS and IL-12. To directly assess the role of IFN-γ in mediating IL-12 enhancement, TI responses in IFN-γ knockout (GKO) mice were examined and it was found that enhancement of IgG2a and IgG3 by IL-12 still occurred in these mice. In fact, IgG3 secretion in response to TI antigen immunization appeared to be totally independent of IFN-γ. In earlier studies using TD antigens (Metzger, D. W., et al., *Eur. J. Immunol.*, 27:1958–1965 (1997))it was similarly found that IL-12 could enhance IgG production in mice genetically deficient in IFN-γ expression. Production of antibody in response to TD antigens was low in GKO mice, but injection of IL-12 significantly enhanced IgG1 and IgG2b levels. In fact, IgG1 levels in some cases were reconstituted by IL-12 to the same levels seen in WT mice. The mechanisms involved in IL-12 enhancement in the absence of IFN-γ are unknown but could involve other intermediary cytokines or a direct stimulation of B cells. It has recently been shown that IL-12 binds to the surface of activated human and murine B cells (Vogel, L. A., et al., *Int. Immunol.*, 8:1955–1962 (1996), which suggests that post-switched cells can respond directly to IL-12, a mechanism that would be consistent with results in both TD and TI antigen systems.

The findings reported herein are significant since S. pneumoniae and N. meningitidis are the leading causes of pneumonia, meningitis and otitis media, causing an estimated 7.5 million cases per year in the U.S. and over 100 million per year worldwide. In addition, the currently available polysaccharide vaccines and conjugate vaccines under development are of limited value particularly in the ability to stimulate isotype switching. The fact that IL-12 induces IgG2a antibodies in response to vaccination is particularly interesting since this is the primary isotype which mediates optimal complement fixation and opsonization in mice. The results described herein were obtained using complete Freund's adjuvant (CFA) and alum, the adjuvant approved for human use, as adjuvant. Furthermore, preliminary analyses of antibody specificities to individual serotypes within the vaccine preparations indicate that high levels of IgG2a are induced against serotypes associated with the most problematic organisms. Robbins et al. (Robbins, J. B., et al., *J. Infect. Dis.*, 171:1387–1398 (1995); Robbins, J. B., et al., *Adv. Exp. Med. Biol.*, 397:169–182 (1996)) have provided evidence that protection against encapsulated bacteria is associated with levels of circulating IgG antibodies, suggesting that serum IgG2a antibodies induced by IL-12 will be effective in mediating bacterial clearance. Thus, the results described herein indicate that IL-12 is useful for increasing the protective capacity of current polysaccharide vaccines as well as conjugate vaccines as they become available.

Thus, the methods and compositions described herein can be used to treat and/or prevent a disease or condition associated with a pathogen having one or more TI antigens. The methods and compositions described herein can utilize an effective amount of IL-12 in combination with a single TI antigen or multiple TI antigens which can be derived from the same pathogen, from different strains of a pathogen or from different pathogens. Thus, the composition comprising IL-12 and one or more TI antigens can be used to prevent and/or treat one or more disease or condition associated with the pathogen(s) from which the TI antigen(s) is derived.

The present invention is illustrated by the following examples, which are not intended to be limiting in any way.

EXEMPLIFICATION

Materials and Methods

Mice

Six- to eight-week old BALB/c and C57BL/6 mice were obtained from the National Cancer Institute (Bethesda, Md.). C57BL/6 TCR β⁻δ⁻ double knockout (KO) mice, CD3ε transgenic mice, (C57BL/6J×CBA/J)F$_1$ mice, and BALB/c IFN-γ KO (GKO) mice were all obtained from Jackson Laboratories (Bar Harbor, Me.). The mice were housed in the animal facility at the Medical College of Ohio and all experimental procedures performed on them adhered to an approved IACUC protocol.

IL-12 Treatment and Immunization Strategy

Recombinant murine IL-12 was provided by Genetics Institute, Cambridge, Mass. IL-12 was stored in aliquots at −80° C. until use. Groups of 3–4 mice were injected intraperitoneally (i.p.) for three consecutive days (days −1, 0, 1) with either 1 μg IL-12 diluted in PBS containing 1% normal mouse serum (PBS-1% NMS) or, as a control, PBS-1% NMS vehicle only. The amounts IL-12 used did not result in any apparent toxicity.

Mice were immunized i.p. on day 0 with antigen precipitated in alum or emulsified in complete Freund's adjuvant (CFA; Gibco BRL, Grand Island, N.Y.) as specified in the Results. Preparation of antigen in alum was performed by mixing 300 μl PBS containing 500 μg of antigen with 160 μl of 10% aluminum potassium sulfate (Fisher Scientific, Pittsburgh, Pa.), adjusting the pH to 6.5, and washing the precipitate three times with PBS. Antigens included 50 μg/mouse of DNP-OVA and DNP-Ficoll (both from Biosearch Technologies Inc., San Rafael, Calif.) as model T-dependent (TD) and T-independent (TI) antigens, respectively. In addition, the following commercial polysaccharide vaccines were used: 1) 115 μg/mouse of PNU-Immune 23 (Lederle Laboratories Division, American Cyanamid Company, Pearl River, N.Y.), a polyvalent pneumococcal vaccine consisting of a mixture of purified capsular polysaccharides from 23 serotypes of *Streptococcus pneumoniae*; and 2) 20 μg/mouse of Menomune-A/C/Y/W-135 (Connaught Laboratories Inc., Swiftwater Pa.), a meningococcal vaccine consisting of purified capsular polysaccharides from 4 serogroups of *Neisseria meningitidis*. In some experiments, mice were boosted i.p. with 115 μg PNU-immune 23 emulsified in incomplete Freund's adjuvant (IFA, Gibco BRL, Grand Island, N.Y.) on day 28. Sera were prepared by bleeding from the orbital plexus.

Detection of Antibody Levels by ELISA

Anti-DNP antibody levels were measured by isotype-specific ELISAs as previously described (Buchanan, J. M., et al., *Int. Immunol.*, 7:1519–1528 (1995); Metzger, D. W., et al., *Eur. J. Immunol.*, 27:1958–1965 (1997)) with some modifications. Briefly, microtiter plates (Nalge Nunc International, Naperville, Ill.) were coated overnight with 10 μg/ml DNP-bovine serum albumin conjugate (DNP-BSA; Biosearch Technologies, Inc.) in PBS. After washing the plates with PBS containing 0.3% Brij-35 (Sigma, St. Louis, Mo.), the plates were blocked with PBS containing 5% fetal calf serum (Hyclone Laboratories, Logan, Utah) and 0.1% Brij-35 (Sigma) for 1 hour at room temperature. The plates were then incubated with serial dilutions of mouse sera for 2 hours at room temperature and bound antibody was detected with alkaline phosphatase which was conjugated to goat anti-mouse Ig (Sigma) for detection of total antibody or to specific goat anti-isotype antibody (Southern Biotechnology Associates, Birmingham, Ala.) for detection of individual isotypes. After incubation at room temperature for 1 hour, p-nitrophenyl substrate was added and color development was read at 405 nm with an ELISA microplate reader (Bio-Tek Instruments Winooski, Vt.). The isotype specificities and appropriate working dilutions of the antibody-enzyme conjugates were determined by titration against standard myeloma proteins of known isotypes (Sigma). Specificity of the assay for DNP was confirmed by lack of binding of the mouse sera to BSA-coated wells.

Antibodies specific for pneumococcal and meningococcal polysaccharides were measured by initially coating microtiter plates at 37° C. for 2 hours with 100 /g/ml polyL-lysine (PLL, Sigma) in PBS. Plates were washed with PBS and 10 μg/ml Pnu-Immune 23 or Menomune A/C/Y/W-135 in PBS was added to each well overnight. The remainder of the assay was performed as described above for anti-DNP antibody measurement. No binding of antisera was observed using plates coated only with PLL.

Statistical Analyses

Statistical analyses were performed using the Mann-Whitney U Test. Titers were calculated by fitting the data to a generalized four parameter logistics curve using Titercal Software.

Cytokine Reverse Transcriptase-PCR (RT-PCR)

Total RNA was isolated from spleens using Trizol reagent (Life Technologies, Inc., Gaithersburg, Mass.). cDNA synthesis was performed using a reverse transcriptase kit (Life Technologies) utilizing oligo $(dT)_{16-18}$ primers. The cDNA was amplified using specific primers for IFN-γ, and hypoxanthine phosphoribosyl transferase (HPRT). The sense and antisense primers had the following sequences: IFN-γ, 5'-TGAACGCTACACACTGCATCTTGG-3' (SEQ ID NO: 1) and 5'-CGACTCCTTTTCCGCTTCCTGAG-3' (SEQ ID NO: 2); HPRT, 5'-GTTGGATACAGGCCAGACTTTGTTG-3' (SEQ ID NO: 3) and 5'-GATTCAACTTGCGCTCATCTTAGGC-3' (SEQ ID NO: 4). PCR amplification was performed by mixing 2 μl of cDNA, 10 μl of 300 mM Tris-HCl (pH 8.5 ), 75 mM $(NH_4)_2SO_4$, 2.0 mM $MgCl_2$, 5 μl of 2.5 mM dNTPs (Invitrogen Corporation), 0.5 μl of Taq DNA polymerase (2.5 U; GIBCO BRL), 2 μl of 20 μM primer, and DEPC water to a final volume of 50 μl. The mixture was incubated at 95° C. for 5 minutes and then subjected to the following amplification profile: 1 minute at 95° C., 1 minute at 56° C. and 1 minute at 72° C. for a duration of 35 cycles. This was followed by a final extension for 10 minutes at 72° C. The PCR products were separated on a 2.5% agarose gel and stained with ethidium bromide. The bands were visualized and photographed under UV transillumination.

Results

IL-12 Enchances DNP-Specific IgG2 a and IgG3 Levels After Immunization With DNP-OVA or DNP-Ficoll IL-12 has been shown to stimulate cell-mediated immunity through increased IFN-γ secretion by T cells and NK cells (Trinchieri, G., Annu. Rev. Immunol., 13:251–276 (1995); Buchanan, J. M. et al., Int. J. Pediat. Hematol. Oncol., 3:123–131 (1996)). However, in that study the effects of IL-12 on humoral immunity was unclear. The ability of IL-12 to significantly enhance the humoral immune response to T-dependent antigens, such as proteins and hapten carrier conjugates has been previously demonstrated (Buchanan, J. M. et al., Intl. Immunol., 7:1519–1528 (1995)). The ability of IL-12 to also enhance antibody responses to T-independent (TI) antigens is now described herein. As described below, the influence of IL-12 on IgG antibody responses to the TI antigen, DNP-Ficoll, was observed and compared to the effects seen with the TD form of DNP conjugated to OVA.

Figure 1B:
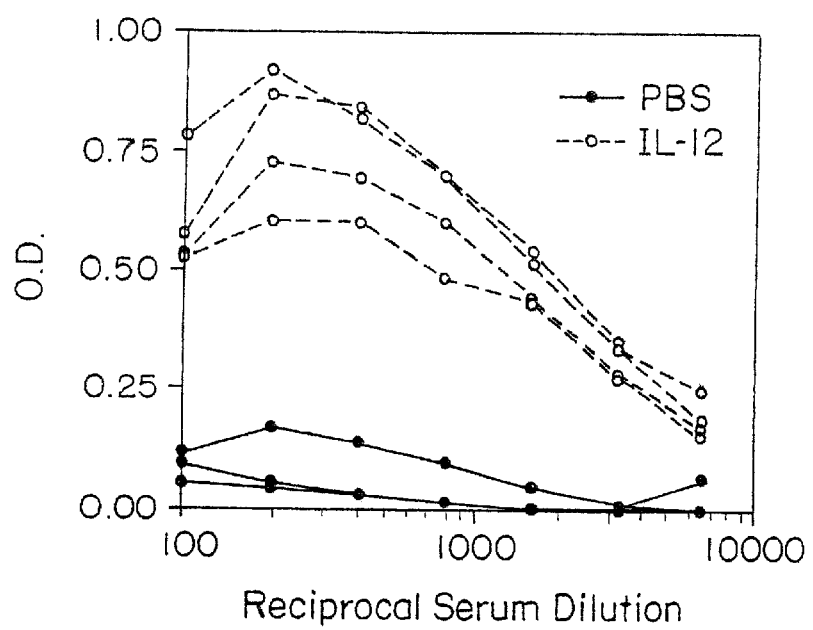
Figure 1C:
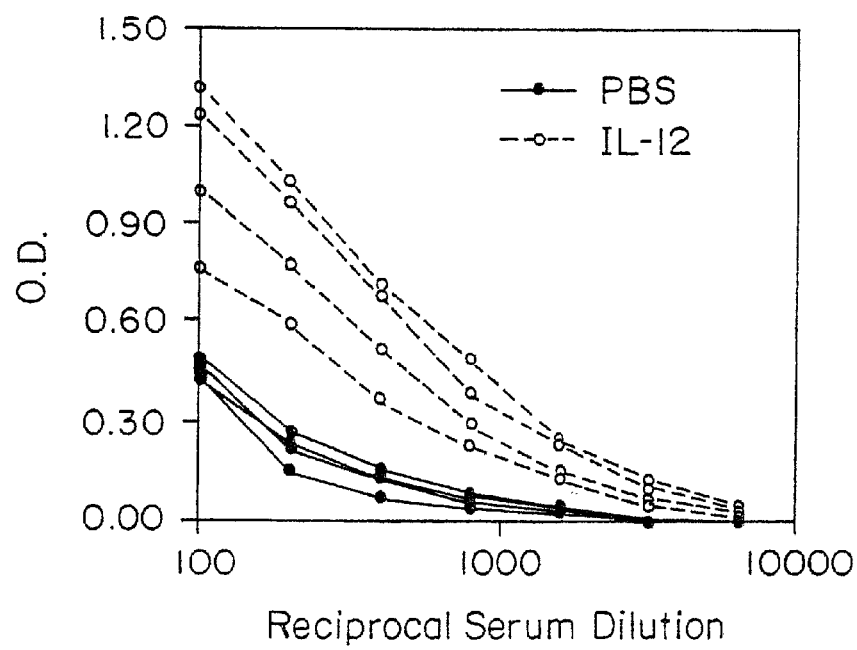
FIGS. 1C–1D are graphs of reciprocal serum dilution versus O.D. showing increased levels of DNP-specific IgG2a (FIG. 1C) and IgG3 (FIG. 1D) in BALB/c mice injected with IL-12 and 50 µg of DNP-Ficoll (open symbols) compared to control mice injected with DNP-Ficoll and PBS (closed symbols); each line represents binding of serum from an individual mouse.
Figure 1D:
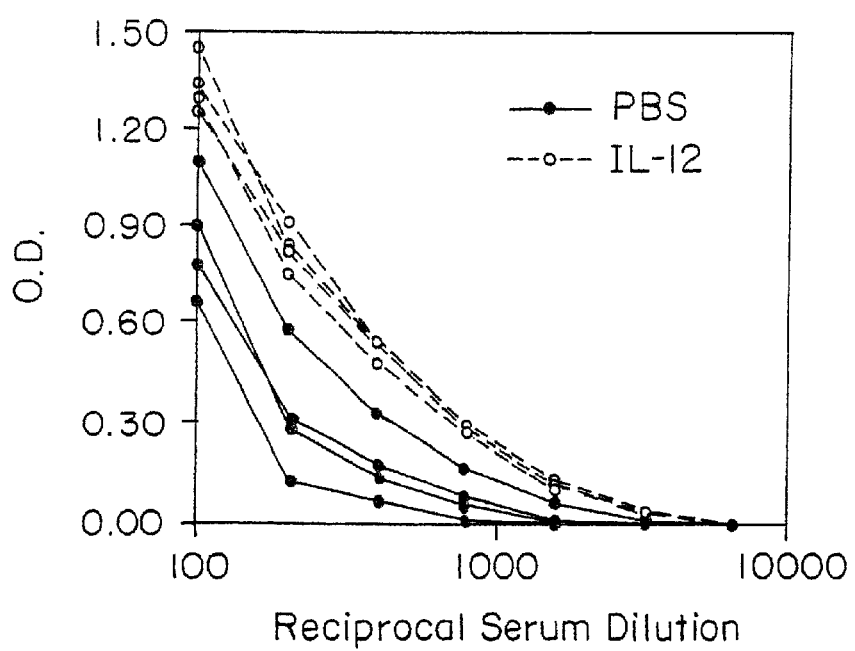

BALB/c mice were injected with 1 μg of IL-12 or PBS vehicle i.p. on days –1, 0, +1 and with DNP-OVA or DNP-Ficoll emulsified in CFA on day 0. It was found that IL-12 treatment of mice during immunization with DNP-OVA caused increased production of serum antibody within 7 days after immunization compared to mice receiving antigen and PBS vehicle. The observed enhancement persisted until at least day 35. Mice immunized with DNP-Ficoll and treated with IL-12 also showed increases in antibody levels, although this effect was not evident until day 21 after immunization. Analysis of individual antibody isotypes revealed increases in the levels of DNP-specific IgG2a and IgG3 in IL-12 treated mice compared to control mice (FIGS. 1A–1D). Significant increases were observed in mice immunized with either the TD or TI forms of DNP, although the effects were most dramatic in the former group. In both cases, the enhancement of IgG2a and IgG3 antibodies reached a maximum on day 21 and remained elevated for at least 3 additional weeks. The results demonstrate that the influence of IL-12 is similar in both TD and TI humoral immune responses and show that IL-12 is an effective adjuvant for TI polysaccharide vaccines.

Figure 2A:
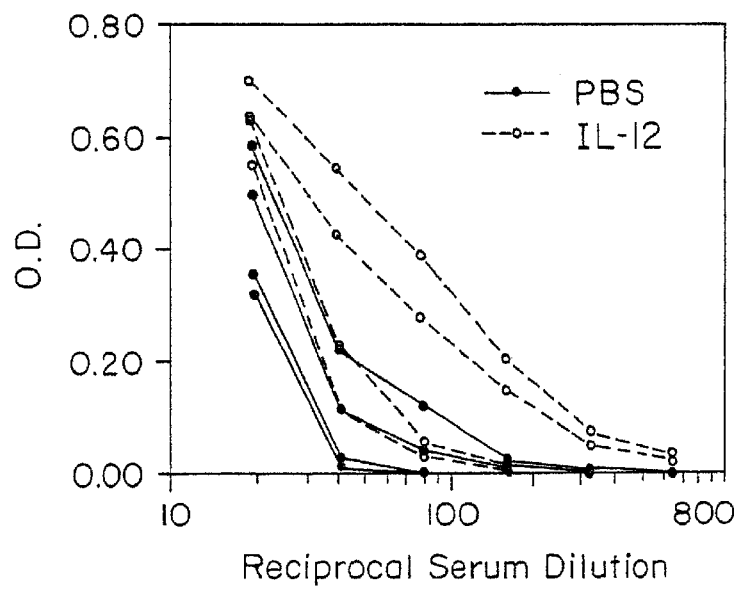
FIGS. 2A–2F are graphs of reciprocal serum dilution versus O.D. showing the effect of treating BALB/c mice with 20 µg of Menomune A/C/Y/W-135 and either IL-12 (open symbols) or PBS vehicle (closed symbols) on total, IgM, IgG2b, IgG1, IgG2a and IgG3 antibody levels; each line represents binding of serum from an individual mouse.
Figure 2B:
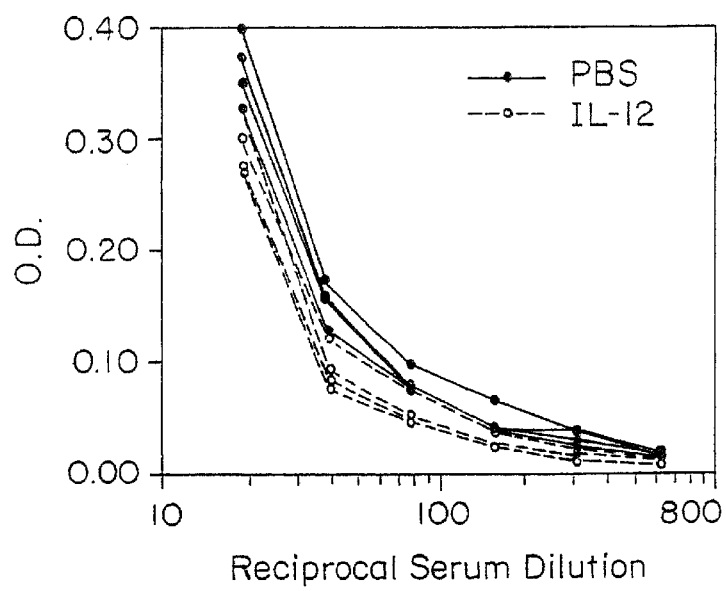
Figure 2C:
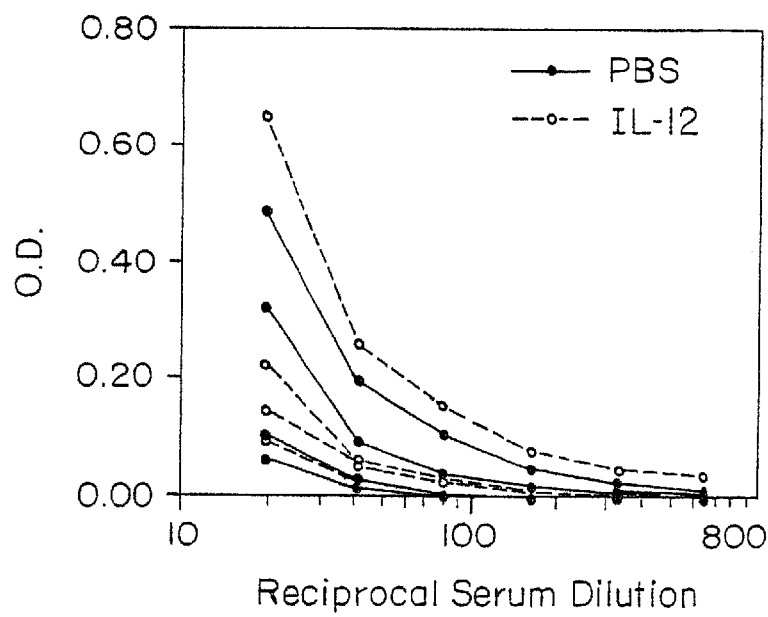
Figure 2D:
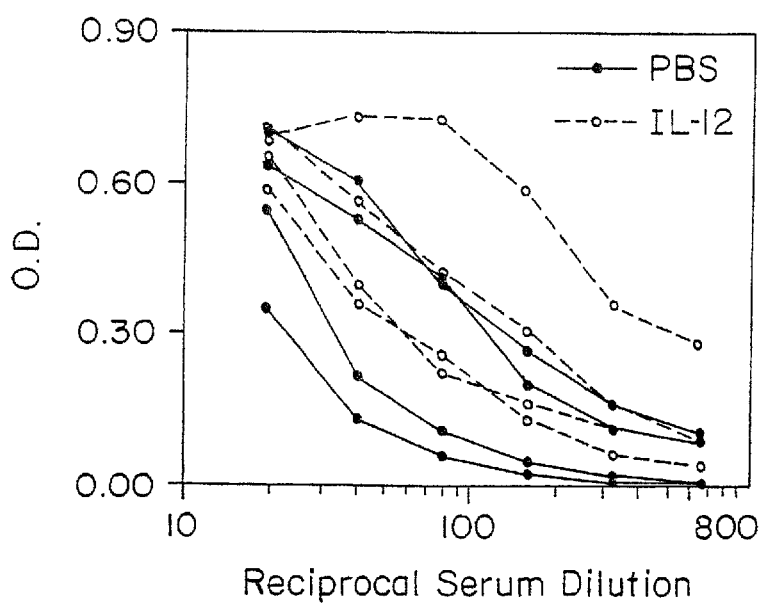
Figure 2E:
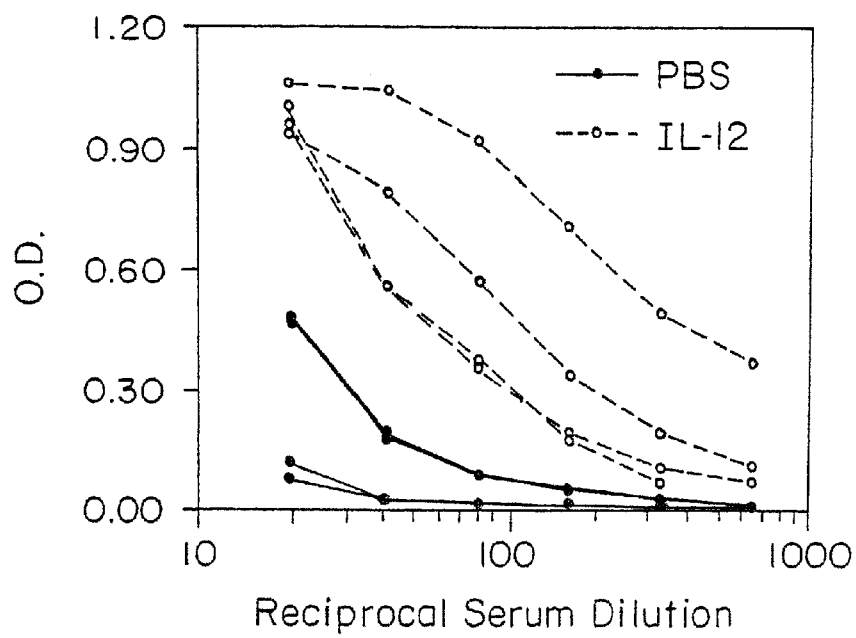
Figure 2F:
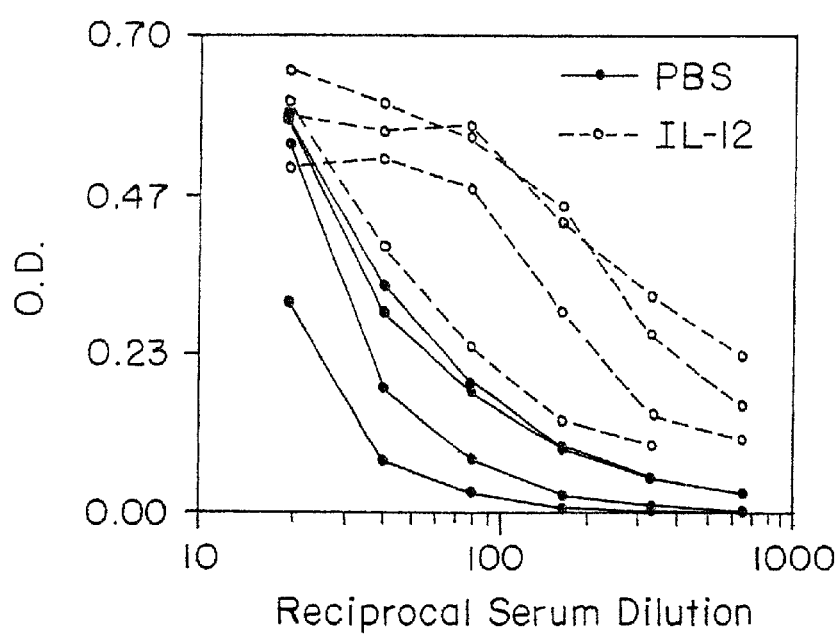

IL-12 Enhances the Humoral Response of Mice to Meningococcal Polysaccharide Vaccine The next series of experiments were performed to determine how IL-12 stimulates IgG antibody responses to other TI antigens, especially polysaccharide antigens that are of medical importance in humans. Experiments were performed using a meningococcal polysaccharide vaccine, a vaccine with limited efficacy in infants. For this purpose, BALB/c mice were immunized with a meningococcal polysaccharide vaccine (Menomune) consisting of the A, C, Y and W-135 capsular serogroups. Vaccine was administered i.p. to adult BALB/c mice together with 3 daily doses of 1 μg IL-12 or PBS vehicle. The mice were bled weekly and tested for polysaccharide-specific antibody of defined isotype by ELISA. It was found that levels of IgG2a and IgG3 anti-polysaccharide antibodies were dramatically enhanced by IL-12 administration compared to mice not exposed to IL-12 (FIGS. 2A–2F). In fact, the mice mounted only very weak or no IgG2a responses unless they had been inoculated with both vaccine and IL-12 . Levels of total and IgG1 antibodies were somewhat increased by IL-12 exposure, IgM was slightly suppressed, and there appeared to be no detectable effect on IgG2b production.

Figure 3A:
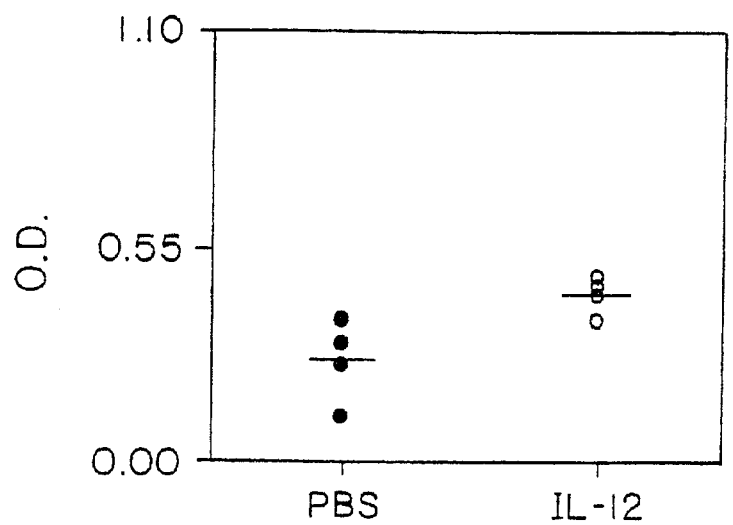
FIGS. 3A–3E are graphs showing the effect of treating BALB/c mice with PNU-Immune and either IL-12 (open symbols) or PBS vehicle (closed symbols) on total, IgM, IgG1, IgG2a and IgG3 antibody levels; each symbol represents binding of serum from an individual mouse.
Figure 3B:
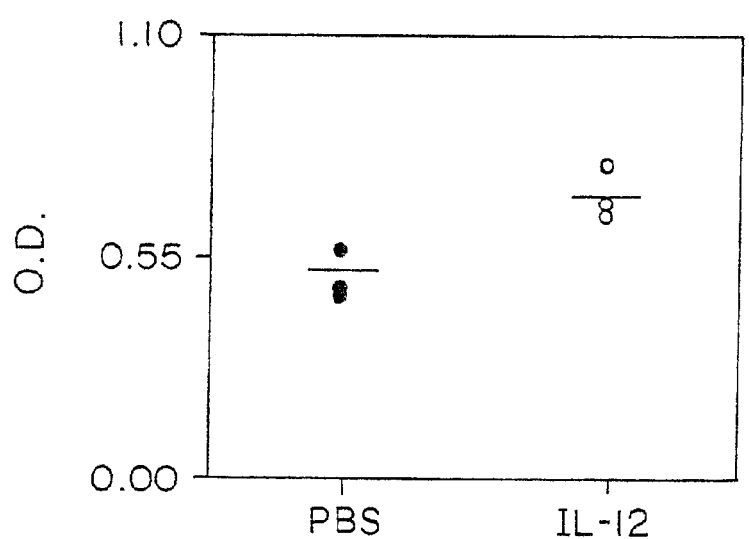
Figure 3C:
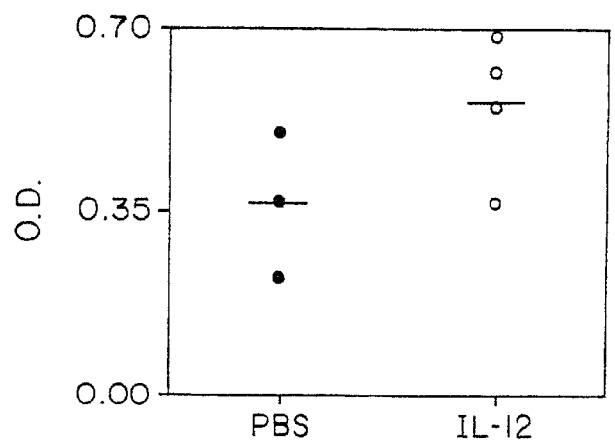
Figure 3D:
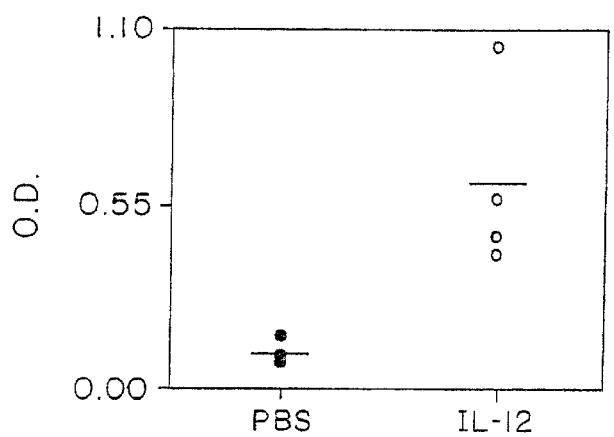
Figure 3E:
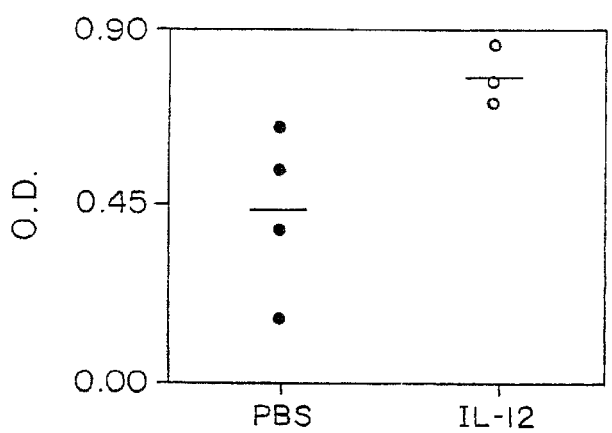

IL-12 Enhances the Humoral Response of Mice to Pneumococcal Polysaccharide Vaccine To test the use of IL-12 as an adjuvant for TI vaccines currently used in humans, mice were immunized with the pneumococcal vaccine, PNU-Immune 23, a mixture consisting of purified capsular polysaccharides from 23 serotypes of S. pneumoniae. On day 0, BALB/c mice were immunized with vaccine emulsified in CFA. On days –1, 0 and +1, the animals were also injected i.p. with IL-12 or 1% PBS vehicle. The mice were boosted i.p. on day 28 with vaccine emulsified in IFA together with IL-12 or 1% NMS on days 27, 28, and 29. Levels of anti-pneumococcal polysaccharide antibodies were measured weekly by ELISA. It was found that mice which were treated with IL-12 had enhanced levels of total antibody compared to controls. Analysis of individual isotypes showed enhanced expression of specific IgM, IgG1, IgG2a and IgG3 (FIGS. 3A–3E). Enhancement of IgG2a was observed as early as day 7 of the primary response, while levels of IgM, IgG1 and IgG3 levels were increased after day 21. IgG2b levels, on the other hand, were undetectable in both IL-12 -treated and control mice throughout the course of the experiment.

Enhancement of IgG2a by IL-12 Occurs in the Absence of T Cells

Figure 4A:
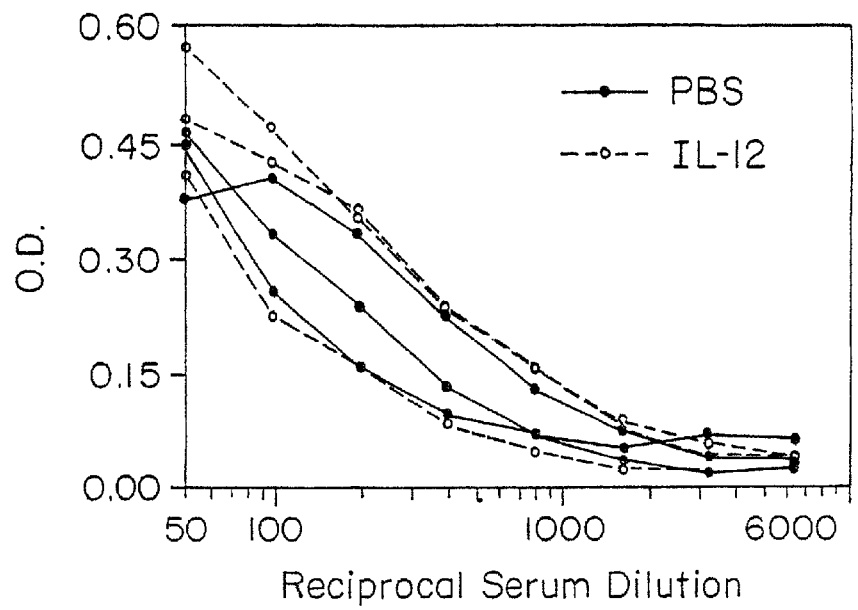
FIGS. 4A–4B are graphs of reciprocal serum dilution versus O.D. showing levels of total and IgG2a antibody levels in C57BL/6 mice treated with DNP-Ficoll and either IL-12 (open symbols) or PBS (closed symbols); each line represents binding of serum from an individual mouse.
Figure 4B:
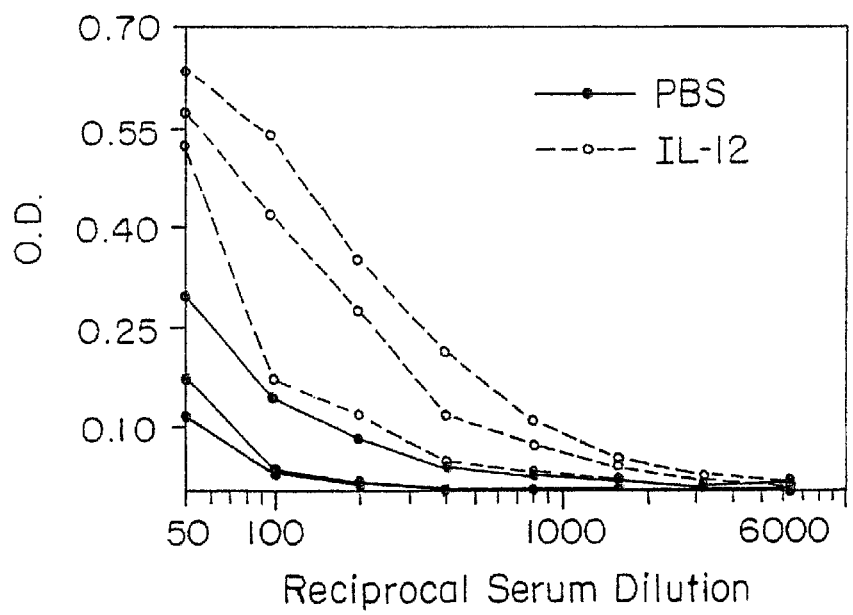
Figure 4C:
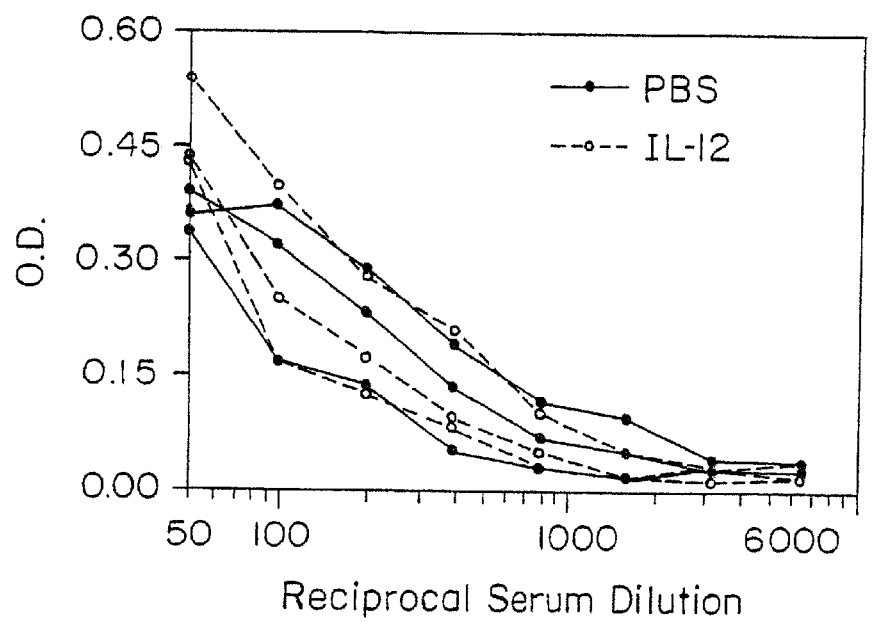
FIGS. 4C–4D are graphs of reciprocal serum dilution versus O.D. showing levels of total and IgG2a antibody levels in C57BL/6 T cell receptor knockout mice specifically lacking T cells (TCR KO mice) treated with DNP-Ficoll and either IL-12 (open symbols) or PBS (closed symbols); each line represents binding of serum from an individual mouse.
Figure 4D:
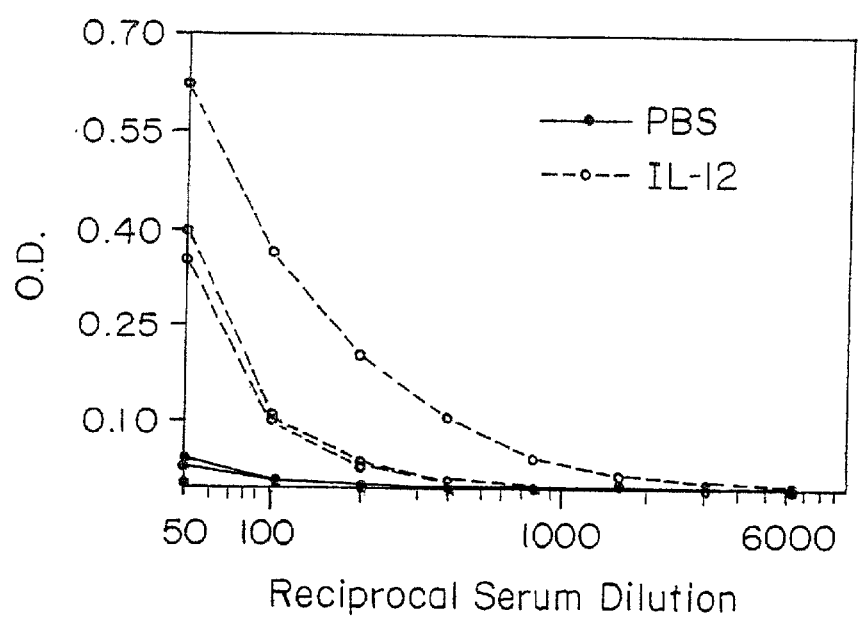

To assess the involvement of T cells in mediating the effects of IL-12 on TI antibody responses, the influence of IL-12 in mice specifically lacking T cells (i.e., C57BL/6 $\beta^-\delta^-$ TCR KO mice) was analyzed. C57BL/6 WT and TCR KO mice were immunized with DNP-Ficoll emulsified in CFA on day 0 and injected i.p. with IL-12 or PBS vehicle on days −1, 0 and +1. Sera were collected weekly and assayed by ELISA for DNP-specific antibodies. The results showed that the levels of WT and TCR KO responses were essentially identical and that IL-12 had little effect on total antibody production in either case (FIGS. 4A–4D). There were also no differences between WT and KO mice in the ability of IL-12 to enhance production of IgG2a DNP-specific antibodies. IgG2a levels were detectable by day 7 and reached maximum levels by day 21. Enhancement by IL-12 was also observed at day 7 and maintained through day 28 in both strains of mice. These results confirm the TI nature of the response and demonstrate that the ability of IL-12 to mediate its effects on TI antibody responses can occur in the absence of T cells. It has previously been shown that activated murine and human B cells express a receptor for IL-12 (Vogel, L. A. et al., Int. Immunol., 8:1955–1962 (1996)) suggesting that IL-12 may directly activate B cells. Alternatively, IL-12 may stimulate natural killer cells to secrete cytokines which then cause the observed effects.

IL-12 Enhances TI Antibody Responses in Mice Lacking Both T and NK Cells

Figure 5A:
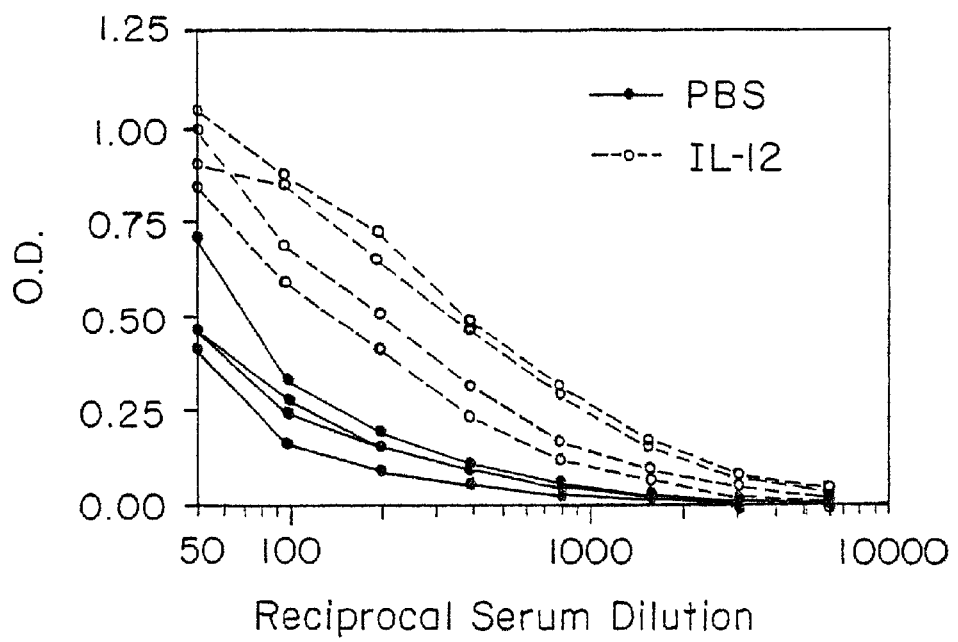
FIGS. 5A–5B are graphs of reciprocal serum dilution versus O.D. showing levels of IgG2a and IgG3 antibody levels in (C57BL/6 ×CBA)$F_1$ control mice treated with DNP-Ficoll and either IL-12 (open symbols) or PBS (closed symbols); each line represents binding of serum from an individual mouse.
Figure 5B:
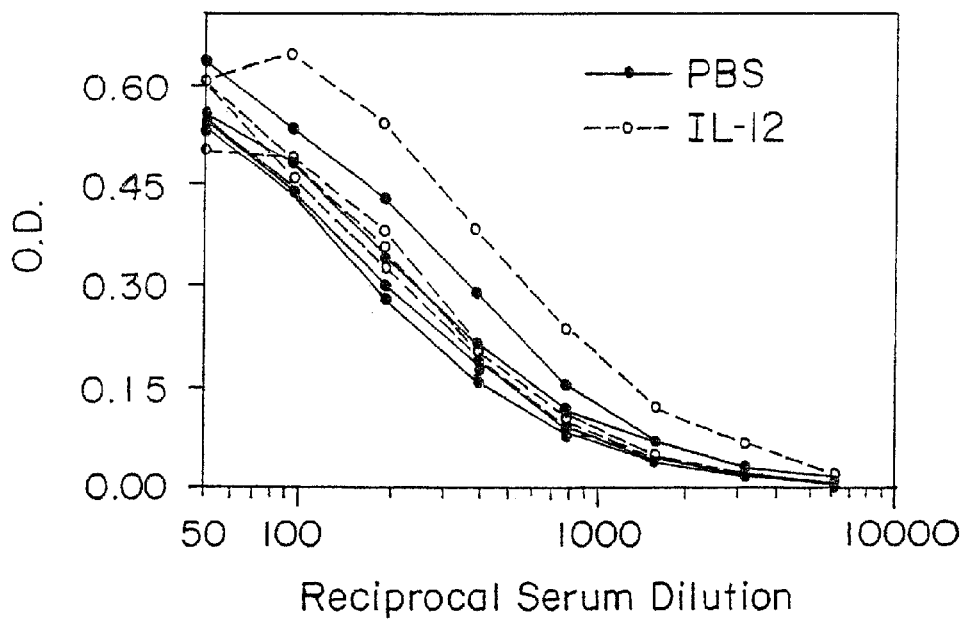
Figure 5C:
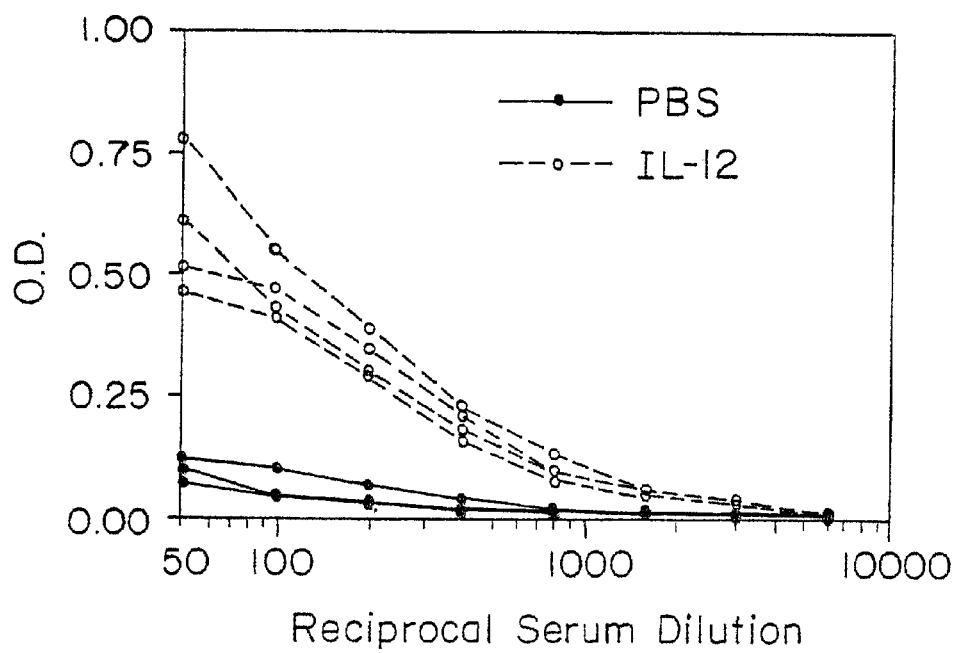
FIGS. 5C–5D are graphs of reciprocal serum dilution versus O.D. showing levels of IgG2a and IgG3 antibody levels in CD3 ε mice lacking T and NK cells treated with DNP-Ficoll and either IL-12 (open symbols) or PBS (closed symbols); each line represents binding of serum from an individual mouse.
Figure 5D:
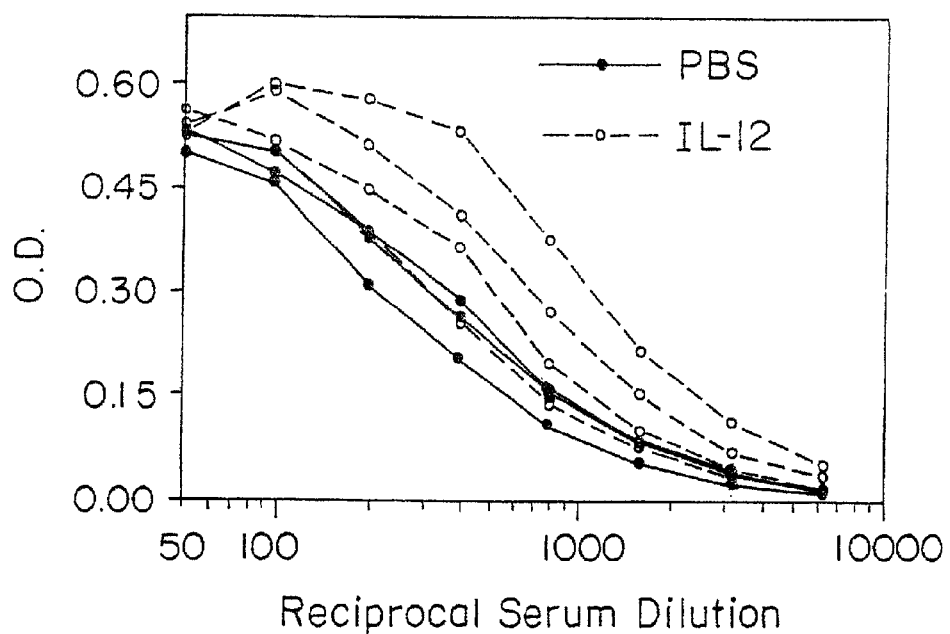

There is evidence that NK cells are responsible for regulating TI antibody responses (Bondada, S. and Garg, M., "Thymus-independent antigens. in Handbook of B and T Lymphocytes., E. C. Snow, ed. Academic Press, San Diego. 343–370 (1994); Snapper, C. M., et al., J. Immunol., 152:4884–4892 (1994); Snapper, C. M., and Mond, J .J., J. Immunol., 157:2229–2233 (1996); Wilder, J. A., et al., J. Immunol., 156:146–152 (1996); Koh, C. Y. and Yuan, D., J. Immunol., 159:4745–4752 (1997)). It is also known that IL-12 activates NK cells (Trinchieri, G., Annu. Rev. Immunol., 13:251–276 (1995); Trinchieri, G., Blood, 84:4008–4027 (1994)). Therefore, to investigate the role of NK cells in the enhancement of IgG2a anti-DNP responses by IL-12, mice which lack both T and NK cells were inoculated with DNP-Ficoll and IL-12. The animals used for this experiment were (C57BL/6×CBA)$F_1$ mice that are transgenic for the human CD3ε gene (Jackson Labs). Introduction of this transgene has led to a complete blockage of both T lymphocyte and NK cell development in the recipient mice but B cell development is normal (Wang, B., et al., Proc. Natl. Acad. Sci., USA, 91:9402–9406 (1994)). Unexpectedly, it was found that exposure of these animals to DNP-Ficoll in the presence of IL-12 resulted in typical enhancement of IgG2a anti-DNP antibody responses (FIGS. 5A–5D). The level of enhancement was actually more striking in CD3ε mice compared to WT controls because of the nearly complete absence of IgG2a antibody produced by CD3ε mice not inoculated with IL-12. Although in this experiment IL-12 showed little enhancement of IgG3 anti-DNP levels in WT mice, it clearly stimulated IgG3 production in CD3ε mice (FIGS. 5A–5D). With regard to other isotypes, IL-12 treatment of WT mice caused reduced production of IgG1 and IgG2b anti-DNP antibody and had no effect on IgM antibody. In CD3ε mice, on the other hand, IL-12 caused suppression of IgM but had no effect on IgG1 and IgG2b levels. Taken together, the results provide evidence that the mechanism of IL-12's influence on IgG2a and IgG3 TI antibody response does not involve NK or T cells, although these cells might influence expression of other isotypes. It has been previously shown that activated B cells express a receptor for IL-12 (Vogel, L. A., et al., Int. Immunol., 8:1955–1962 (1996)), suggesting that IL-12 directly activates B cells. Alternatively, IL-12 could stimulate secretion of intermediary cytokines from cells other than T or NK cells and these cytokines may then mediate the observed effects.

Enhancement of TI Antibody Production by IL-12 is Only Partially Dependent on IFN-γ

IFN-γ induced by IL-12 plays a pivotal role in enhancement of IgG2a and IgG3 during TD immune responses (Germann, T, et al., Eur. J. Immunol., 25:823–829 (1995); Buchanan, J. M., et al., Int. Immunol., 7:1519–1528 (1995); Metzger, D., et al., Eur. J. Inmunol., 27:1958–1965 (1997)). To investigate the role of IFN-γ in stimulating IgG2a and IgG3 antibody production during TI responses, BALB/c mice were immunized with DNP-Ficoll and injected with either PBS vehicle or IL-12 as described above. Analysis of splenic mRNA 12 hours later revealed that IFN-γ levels were substantially increased after exposure to IL-12. The results were identical regardless of whether alum or CFA was used as an adjuvant. The ability of IL-12 to induce large amounts of IFN-γ MRNA during a TI response suggests that IFN-γ is important in the observed enhancement of antibody production.

To directly elucidate the importance of IFN-γ, WT and GKO mice were immunized with Menomune or DNP-Ficoll and simultaneously injected with either PBS vehicle or IL-12. WT mice treated with antigen and IL-12 has a three- to ten- fold enhancement of serum IgG2a levels in comparison to mice that received only antigen and PBS vehicle (the Table). GKO mice immunized in the same manner showed less enhancement but still tended to have increases in levels of IgG2a (approximately two-fold increases). In the case of IgG3, two to three-fold enhancement by IL-12 was observed in both WT and GKO mice, except that GKO mice immunized with DNP-Ficoll produced large amounts of IgG3 antibody regardless of whether they were treated with IL-12 or PBS vehicle. These results suggest that enhancement of IgG2a by IL-12 is partially but not completely dependent on IFN-γ whereas the increase in levels of IgG3 is wholly IFN-γ independent.

Enhancement of TI Antibody Responses by IL-12 is Only Partially IFN-γ-Dependent

| Antibody Isotype | In vivo treatment | WT mean titer* | GKO mean titer |
|---|---|---|---|
| IgG2a | Menomune + PBS | 25 (0, 18, 22, 59) | 23 (0, 29, 31, 33) |
|  | IL-12 | 243+ (70, 112, 266, 525) | 48 (20, 43, 47, 82) |
|  | DNP-Ficoll + PBS | 61 (48, 60, 65, 69) | 57 (43, 47, 55, 83) |
|  | IL-12 | 193+ (101, 123, 147, 402) | 111 (52, 76, 113, 201) |
| IgG3 | Menomune + PBS | 250 (110, 179, 260, 452) | 197 (102, 165, 203, 317) |
|  | IL-12 | 626+ (316, 625, 650, 911) | 498+ (310, 482, 558, 643) |
|  | DNP Ficoll + PBS | 473 (328, 430, 497, 637) | 794 (342, 443, 474, 1915) |

-continued

| Antibody Isotype | In vivo treatment | WT mean titer* | GKO mean titer |
|---|---|---|---|
| | IL-12 | 740<br>(323, 497, 825, 1313) | 729<br>(443, 544, 631, 1298) |

*Groups of four BALB/C WT and GKO mice were immunized with Menomune or DNP-Ficoll in CFA on day 0 and treated with PBS vehicle of IL-12 on days −1, 0 and +1. Two weeks later the sera were assayed for antibody levels by ELISA using plates coated with Menomune or DNP-BSA, respectively. The results are expressed as an average titer for each group of mice with the individual titers shown in parentheses. +$p < 0.05$ compared to mice injected with antigen or PBS Equivalents While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

We claim:

1. A method of inducing a T-cell independent immune response to a T-cell independent antigen in a host, which comprises administering to the host an effective amount of interleukin-12 and the T-cell independent antigen, but not T cells, wherein administration of the interleukin-12 and the antigen results in a T-cell independent immune response to the antigen in the host.

2. The method of claim 1 wherein the T-cell independent antigen is selected from the group consisting of: a carbohydrate, a lipid, a glycolipid, a carrier conjugate, a lipopolysaccharide and a phage.

3. The method of claim 2 wherein the carbohydrate antigen is a polysaccharide antigen.

4. The method of claim 3 wherein the polysaccharide antigen is selected from the group consisting of: a bacterial capsular antigen and a bacterial cell wall antigen.

5. The method of claim 1 wherein the T-cell independent antigen is from bacteria selected from the group consisting of: *Streptococcus pneumoniae, Neisseria meningiditis* and *Haemophilus influenzae.*

6. The method of claim 1 wherein the immune response is a humoral immune response.

7. The method of claim 6 wherein the humoral immune response results in an enhanced IgG2a and IgG3 antibody response.

8. A method of enhancing a T-cell independent immune response against a T-cell independent antigen in a host, which comprises administering to the host an effective amount of interleukin-12 and the T-cell independent antigen, but not T cells, wherein administration of the interleukin-12 and the antigen results in an enhanced T-cell independent immune response to the antigen in the host.

9. The method of claim 8 wherein the T-cell independent antigen is selected from the group consisting of: a carbohydrate, a lipid, a glycolipid, a carrier conjugate, a phosphorylcholine, a lipopolysaccharide and a phage.

10. The method of claim 9 wherein the carbohydrate antigen is a polysaccharide antigen.

11. The method of claim 10 wherein the polysaccharide antigen is selected from the group consisting of: a bacterial capsular antigen and a bacterial cell wall antigen.

12. The method of claim 8 wherein the T-cell independent antigen is from bacteria selected from the group consisting of: *Streptococcus pneumoniae, Neisseria meningiditis* and *Haemophilus influenzae.*

13. The method of claim 8 wherein the immune response is a humoral immune response.

14. The method of claim 13 wherein the humoral immune response results in an enhanced IgG2a and IgG3 antibody response.

15. A method of inducing a T-cell independent immune response to *Streptococcus pneumoniae* in a host, which comprises administering to the host an effective amount of interleukin-12 and a T-cell independent antigen of *Streptococcus pneumonia,* but not T cells.

16. The method of claim 15 wherein the immune response is a humoral immune response.

17. The method of claim 16 wherein the humoral immune response results in an enhanced IgG2a and IgG3 antibody response.

18. A method of inducing an immune response to *Neisseria meningitidis* in a host, which comprises administering to the host an effective amount of interleukin-12 and a T-cell independent antigen of *Neisseria meningitidis,* but not T cells.

19. The method of claim 18 wherein the immune response is a humoral immune response.

20. The method of claim 19 wherein the humoral immune response results in an enhanced IgG2a and IgG3 antibody response.

21. A composition comprising interleukin-12 and a T-cell independent antigen, but not T cells in a pharmaceutically acceptable carrier wherein the interleukin-12 and the T-cell independent antigen enhance a T-cell independent immune response against the T-cell independent antigen.

22. The composition of claim 21 wherein the T-cell independent antigen is selected from the group consisting of: a carbohydrate antigen, a lipid antigen, a glycolipid antigen, a carrier conjugate antigen, a phosphorylcholine antigen, a lipopolysaccharide antigen and a phage antigen.

23. The composition of claim 22 wherein the carbohydrate antigen is a polysaccharide antigen.

24. The composition of claim 23 wherein the polysaccharide antigen is selected from the group consisting of: a bacterial capsular antigen and a bacterial cell wall antigen.

25. The composition of claim 21 wherein the T-cell independent antigen is from bacteria selected from the group consisting of: *Streptococcus pneumoniae, Neisseria meningiditis* and *Haemophilus influenzae.*

* * * * *